United States Patent [19]

Saito et al.

[11] Patent Number: 4,864,062
[45] Date of Patent: Sep. 5, 1989

[54] PROCESS FOR PRODUCING DIOCTAMETHYLENE TRIAMINE

[75] Inventors: Masao Saito, Chiba; Koichiro Yamada, Niigata, both of Japan

[73] Assignee: Mitsubishi Gas Chemical Company, Inc., Tokyo, Japan

[21] Appl. No.: 249,002

[22] Filed: Sep. 23, 1988

[30] Foreign Application Priority Data

Sep. 24, 1987 [JP] Japan ................................ 62-237272

[51] Int. Cl.$^4$ ............................................. C07C 87/20
[52] U.S. Cl. ................................................. 564/512
[58] Field of Search ................ 564/512, 511, 470; 502/79

[56] References Cited

U.S. PATENT DOCUMENTS

| | | | |
|---|---|---|---|
| 3,391,127 | 7/1968 | Kamel | 564/511 |
| 4,277,622 | 7/1981 | Asada et al. | 564/512 |
| 4,547,591 | 10/1985 | Brennan et al. | 564/479 |

FOREIGN PATENT DOCUMENTS

| | | |
|---|---|---|
| 0013554 | 7/1980 | European Pat. Off. . |
| 0212287 | 3/1987 | European Pat. Off. . |
| 92348 | 7/1980 | Japan . |
| 0339645 | 3/1983 | Japan . |
| 0239442 | 11/1985 | Japan . |
| 0239443 | 11/1985 | Japan . |

*Primary Examiner*—Robert T. Bond
*Assistant Examiner*—Peter G. O'Sullivan
*Attorney, Agent, or Firm*—Browdy and Neimark

[57] ABSTRACT

A process for producing dioctamethylene triamine is disclosed which comprises dimerizing octamethylene diamine in the presence of a zeolite catalyst, characterized in that the catalyst is represented by the formula:

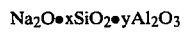

$$Na_2O \bullet xSiO_2 \bullet yAl_2O_3$$

wherein x and y are so selected that the molar ratio of $Na_2O$ to $Al_2O_3$ is in the range of 0.02 to 0.05 and the molar ratio of $SiO_2$ to $Al_2O_3$ is in the range of 1 to 10.

8 Claims, No Drawings

PROCESS FOR PRODUCING DIOCTAMETHYLENE TRIAMINE

BACKGROUND OF THE INVENTION

This invention relates to a process for producing 1,17-diamino-9-azaheptadecane (dioctamethylene triamine) (hereinunder referred to as "triamine") which is useful as an intermediate for agricultural agents.

The triamine may be used as an intermediate for synthesizing guazatin, an agricultural agent which is useful as an agricultural bactericide and has antibacterial properties relative to plant pathogenic bacteria.

PRIOR ART

U.S. Pat. No. 4,277,622 and patent publication (Kokai) No. 60-239442 discloses a process for producing triamine which comprises dimerizing octamethylene diamine (hereinunder referred to as "diamine").

U.S. Pat. No. 4,277,622 discloses a process for producing triamine which comprises adding an acid catalyst, such as nitric acid, hydrochloric acid, a hydrogen chloride gas, p-toluene sulfonic acid, sulfanilic acid or the like, to the diamine and heating the mixture. However, this process has the following shortcomings:
(i) Strong acids, such as nitric acid must be used;
(ii) The dimerization of the diamine in the presence of the acid catalyst must be carried out at about 200° C. for a period of more than 5 hours;
(iii) Since sodium hydroxide must be used for recovering the resulting triamine from the mixture of the triamine and the acid, a large amount of waste liquor has to be discharged.

Publication No. 60-239442 discloses a process for producing triamine which comprises dimerizing the diamine in the presence of a Raney catalyst and in the absence of any solvent. However, not only does the process necessitate use of the expensive Raney catalyst, but when the diamine is heated in the presence of a Raney catalyst, deammoniation is caused such as to dimerize the diamine, and because in this process, successive reaction is normally caused, such as trimerization of the diamine, or polymerization thereof, the dimerization of the diamine needs to be carried out while a maintaining the degree of conversion of the diamine at a level below 50% in order to prevent a successive reaction of this sort. This inevitably lowers the yield of triamine.

SUMMARY OF THE INVENTION

The present inventors have made wide-ranging research with a view to producing triamine more effectively and have found that if diamine is dimerized in the presence of a zeolite catalyst having a specific ratio between $Na_2O$, $SiO_2$ and $Al_2O_3$, triamine can be obtained in a high yield and with a high rate of selectivity.

This invention relates to a process for producing dioctamethylene triamine which comprises dimerizing octamethylene diamine in the presence of a zeolite catalyst, characterized in that the catalyst is represented by the formula:

$$Na_2O \bullet xSiO_2 \bullet yAl_2O_3$$

wherein x and y are so selected that the molar ratio of $Na_2O$ to $Al_2O_3$ is in the range of 0.02 to 0.5 and preferably 0.1 to 0.4, and the molar ratio of $SiO_2$ to $Al_2O_3$ is in the range of 1 to 10 and preferably 2 to 8.

DETAILED DESCRIPTION OF THE INVENTION

The reaction of this invention is carried out as shown in the following:

$$2H_2N(CH_2)_8NH_2 \rightarrow H_2N(CH_2)_8NH(CH_2)_8NH_2 + NH_3$$

Usually, the zeolite catalyst employed in this invention may contain about 70-80% by weight of $SiO_2$, about 15-25% by weight of $Al_2O_3$ and about 1-5% by weight of $Na_2O$ on an anhydrous basis, and may have a usable pore size of about 8 Å. It is preferably that the X-ray diffraction of the zeolite catalyst powder has an intensity of no higher than $I/I_1 = 14.3$, 6.66 and 3.76 dÅ when measured at 5°–105° (2θ). For example, Y-type natural zeolite such as Faujasite is preferred.

The present reaction may be carried out using the following processes:
(i) the diamine is mixed with the zeolite catalyst powder to form a slurry, followed by dimerizing the diamine; or
(ii) the diamine is passed through the bed of the zeolite catalyst to dimerize the diamine.

In process (i), the amount of catalyst employed may be in the range of 0.5–5.0% by weight and preferably 1.0–4.0% by weight on the basis of the weight of diamine. When the catalyst is used in an amount of more than 5% by weight, the reaction proceeds too rapidly so that by-products are produced. This lowers the selectivity to triamine. When the catalyst is used in an amount of less than 0.5% by weight, the reaction speed becomes slow. This lowers the reactivity of the diamine and the yield of triamine.

The reaction temperature may be in the range of 275°–330° C. and preferably 280°–320° C. High boiling point materials such as polyamine are likely to be formed at a temperature above 330° C., and both the reactivity of the diamine and the yield of triamine are lowered at a temperatures below 275° C. The reaction pressure depends on the reaction temperature, but is preferably in the range of 5–20 kg/cm² for the temperatures mentioned above.

The reaction time should be in the range of 0.5–3 hours, and preferably 1–2.5 hours. If the reaction time is too short, the reaction and yield are lowered. If it is too long, an excessive amount of polyamine is formed.

The reaction mixture formed by a "slurry process" is cooled to room temperature and depressurized to atmospheric pressure. Then the mixture is washed with a solvent, such as an alcohol, an ether or an ester capable of dissolving the reactive product. The catalyst powder is separated from the mixture by a centrifugal separator. The resulting solution comprises triamine, unreacted diamine and solvents. The triamine is separated from the mixture by a vacuum distillation. The distillation would usually be effected at a pressure of 0.1–10 Torr and a temperature of 120°–200° C.

The advantages of the present invention are as follows:
(1) An inexpensive zeolite can be used as the catalyst; and triamine can be obtained in high yield and selectivity while the production of economically valueless polyamines is small.

(2) According to the present invention, the reaction can be carried out by mixing the diamine with the catalyst powder to form a slurry. In this process, the catalyst powder can be separated from the reaction mixture by centrifuge, and the solvent and the unreacted diamine can be separated by vacuum distillation. Thus, purification of the reaction product is easy.

(3) Use of an expensive catalyst is unnecessary. Since no strong acid is used, treatment of waste liquor becomes unnecessary.

Consequently, the cost of production is low. The industrial significance of this invention is very high.

The present invention is further illustrated by the following non-limiting Examples and Comparative runs.

All percentages and parts in these Examples and Control Runs are by weight, unless otherwise specified.

EXAMPLE 1

A 100 ml stainless steel autoclave was purged with nitrogen. The diamine (raw material) (10 gram: 0.0694 mol) was charged into the autoclave. Commercially available natural zeolite catalyst in the form of Faujasite ($SiO_2$ to $Al_2O_3=5.7$ and $Na_2O$ to $Al_2O_3=0.3$; 0.2 g) was added to diamine, and the autoclave was then sealed. The autoclave was set in a shaking apparatus. The autoclave was shaken for 2 hours while its internal temperature was maintained at 298° C. The internal pressure of the autoclave rose to 10 kg.cm$^2$ during this period. After the reaction had completed, the autoclave was cooled to room temperature and the generated ammonia gas was discharged. The contents of the autoclave were washed with methanol and the catalyst powder was separated from the contents by centrifuge. Gas chromatographic analysis showed the reactivity of diamine to be 42%, the yield of triamine to be 40% and the selectivity to triamine to be 96%.

EXAMPLE 2

The procedure of Example 1 was repeated in the same manner except that 0.5 g of the catalyst was used. Gas chromatographic analysis showed that the reactivity of diamine was 75%, the yield of triamine 36% and the selectivity to triamine 48%.

Examples 1 and 2 show that when the amount of catalyst employed is increased, though the reactivity is increased, selectively is lowered.

EXAMPLE 3

The procedure of Example 1 was repeated in the same manner except that the internal temperature of the autoclave was 312° C. The internal pressure of the autoclave rose to 12 kg/cm$^2$ during the period. The results were as follows:

| | |
|---|---|
| Reactivity of diamine | 70% |
| Yield of triamine | 42% |
| Selectivity to triamine | 60% |

EXAMPLE 4

The procedure of Example 1 was repeated in the same manner except that the internal temperature of the autoclave was 280° C. The internal pressure of the autoclave rose to 4 kg/cm$^2$ during the period. The results were as follows:

| | |
|---|---|
| Reactivity of diamine | 15% |
| Yield of triamine | 14.7% |
| Selectivity to triamine | 98% |

CONTROL RUN 1

The procedure of Example 1 was repeated except that Mordenite ($SiO_2$ to $Al_2O_3=14.9$ and $Na_2O$ to $Al_2O_3=0.01$), Offretite ($SiO_2$ to $Al_2O_3=8.0$ and $K_2O$ to $Al_2O_3=0.25$) or Ferrierite ($Si_2O$ to $Al_2O_3=17.0$ and $K_2O$ to $Al_2O_3=0.05$) were used. The activity of these catalysts was low, and the diamine was only slightly dimerized.

What is claimed is:

1. A process for producing dioctamethylene triamine which comprises dimerizing octamethylene diamine in the presence of a zeolite catalyst, characterized in that the catalyst is represented by the formula:

$$Na_2O \bullet xSiO_2 \bullet yAl_2O_3$$

wherein x and y are so selected that the molar ratio of $Na_2O$ to $Al_2O_3$ is in the range of 0.02 to 0.5 and the molar ratio of $SiO_2$ to $Al_2O_3$ is in the range of 1 to 10.

2. The process of claim 1, wherein the molar ratio of $Na_2O$ to $Al_2O_3$ is in the range of 0.1-0.4 and the molar ratio of $SiO_2$ to $Al_2O_3$ is in the range of 2-8.

3. The process of claim 1, wherein the catalyst contains about 70-80% by weight of $SiO_2$, about 15-25% by weight of $Al_2O_3$ and about 1-5% by weight of $Na_2O$ on an anhydrous basis.

4. The process of claim 1, wherein the dimerization of octamethylene diamine is carried out by heating the mixture of the diamine and the catalyst.

5. The process of claim 1, wherein the catalyst is Y-type natural zeolite.

6. The process of claim 4, wherein the zeolite is Faujasite.

7. The process of claim 1, wherein the dimerization reaction temperature is in the range of 275°-330° C.

8. The process of claim 1, wherein the reaction time is in the range of 0.5-3 hours.

* * * * *